(12) United States Patent
Major et al.

(10) Patent No.: US 8,354,560 B2
(45) Date of Patent: Jan. 15, 2013

(54) PROCESS FOR PRODUCING NITROALCOHOLS

(75) Inventors: Michael D. Major, Evanston, IL (US); David W. Moore, Hebron, IL (US)

(73) Assignee: Rohm and Haas Company, Philadelphia, PA (US)

( * ) Notice: Subject to any disclaimer, the term of this patent is extended or adjusted under 35 U.S.C. 154(b) by 150 days.

(21) Appl. No.: 12/927,016

(22) Filed: Nov. 4, 2010

(65) Prior Publication Data

US 2011/0105804 A1    May 5, 2011

Related U.S. Application Data

(60) Provisional application No. 61/280,577, filed on Nov. 5, 2009.

(51) Int. Cl.
*C07C 29/48* (2006.01)
(52) U.S. Cl. ........................................... 568/704
(58) Field of Classification Search .................. 568/704
See application file for complete search history.

(56) References Cited

U.S. PATENT DOCUMENTS

| | | |
|---|---|---|
| 2,151,517 A | 7/1938 | Kamlet |
| 5,041,691 A | 8/1991 | Wuest et al. |
| 5,750,802 A | 5/1998 | Baxter, Jr. et al. |
| 5,962,737 A | 10/1999 | West |

OTHER PUBLICATIONS

Bhattacharya, A., et al, Environmentally Solvent-Free Processes: Novel Dual Catalyst System in Henry Reaction, Org. Process Res. & Devel, 2003, 7, pp. 254-258.
Ballini, R., et al., Nitroaldol Reaction in Aqueous Media: An Important Improvement on the Henry Reaction, J. Org. Chem. (1997) 62, pp. 425-427.
Ballini, R., et al., Recent Developments on the chemistry of aliphatic nitro compounds under aqueous medium, Green Chem., 2007, 9, pp. 823-838.
Reddy, K.R., et al., Zinc-Proline Complex: An Efficient, Reusable Catalyst for Direct Nitroaldol Reaction in Aqueous Media, Synthetic Communications, (2007)37:12, pp. 1971-1976.
Luzzio, F.A., Tetrahedron Report No. 553: The Henry reaction: recent examples, Tetrahedron 57, 2001 pp. 915-945.
Phukan, M., et al., Imidazole-Catalyzed Henry Reactions in Aqueous Medium, Synthetic Communications, (2008) 38:18, pp. 3068-3073.
Masayuki, F., "A Highly Chemoselective Reduction of Conjugated Nitro Olefins with . . . ", Bulletin of the Chemical Society of Japan, vol. 61, Nov. 1988, pp. 4029-4035.

*Primary Examiner* — Sikarl Witherspoon
(74) *Attorney, Agent, or Firm* — Marcella M. Bodner

(57) ABSTRACT

Nitroaldol ("Henry") reactions between nitroalkanes and aldehydes in the presence of a catalyst and a two-phase reaction medium produce nitroalcohols at increased reaction rates compared to single-phase organic solvent systems, and do not require use of surfactants as is typical of single-phase aqueous solvent systems and solventless systems. The reaction medium comprises an organic solvent phase and an aqueous solvent phase. The aqueous solvent may be 100% water.

7 Claims, 1 Drawing Sheet

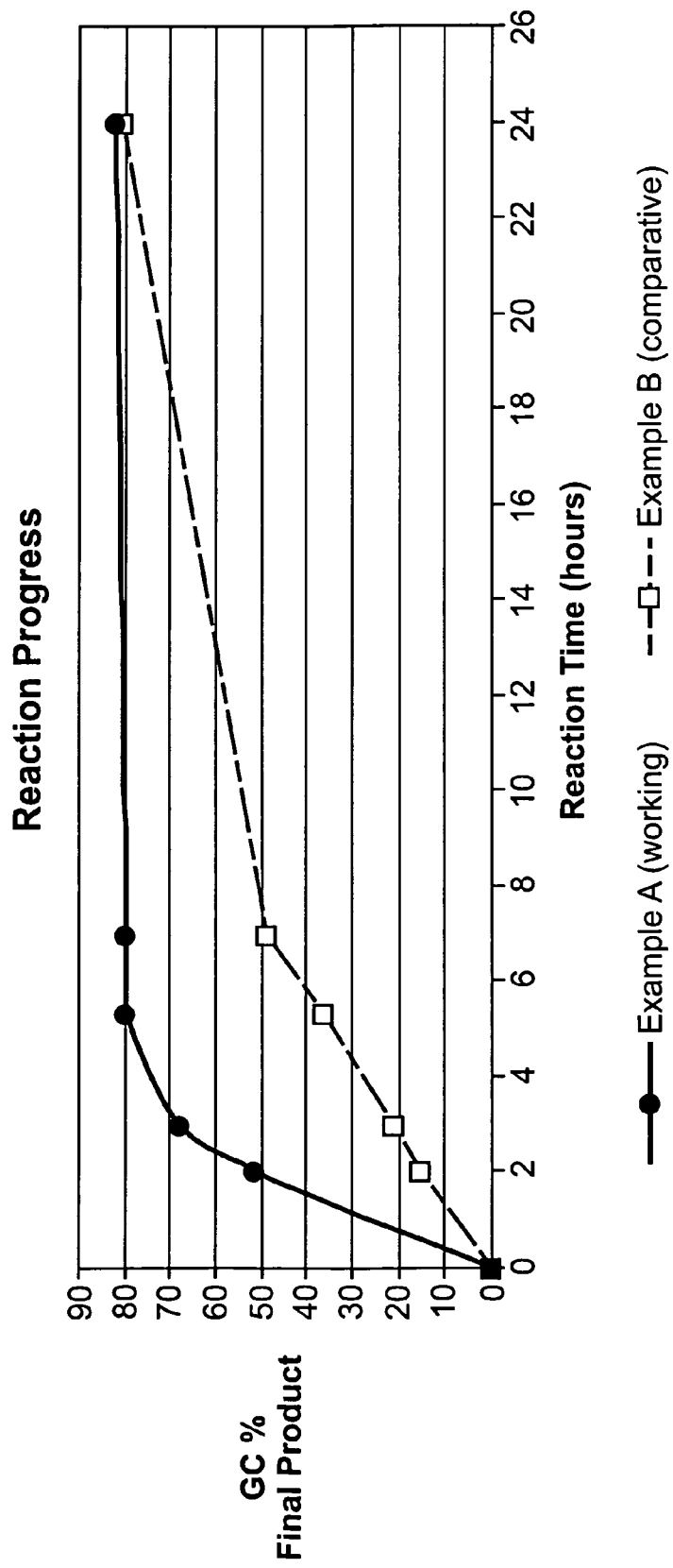

PROCESS FOR PRODUCING NITROALCOHOLS

This application claims the benefit of priority under 35 U.S.C. §119(e) of U.S. Provisional Patent Application No. 61/280,577 filed on Nov. 5, 2009.

FIELD OF THE INVENTION

The present invention relates to a process for producing nitroalcohols by nitroaldol reaction of nitroalkanes and aldehydes in the presence of a catalyst and a two-phase reaction medium.

BACKGROUND OF THE INVENTION

Nitroalcohols are useful intermediates in organic synthesis for various transformations, especially in the synthesis of 1,2-amino alcohols. The nitroaldol reaction (Henry reaction) involves base-catalyzed addition of nitroalkanes to a carbonyl compound, such as an aldehyde. Certain nitroaldol processes, such as that for producing 3-nitro-4-octanol from 1-nitropropane and valeraldehyde in the presence of an amine, are unacceptably slow from a commercial (economic) standpoint. In particular, even after several hours of reaction time, and even in the presence of large amounts of catalyst, the reaction between 1-nitropropane and valeraldehyde was not complete, or was completed with insufficient purity for further commercial use. Thus, there is a need for a method to improve certain nitroaldol reaction processes in terms of rate and/or purity There are catalysts that may increase the rate of reaction in a similar manner; however, they are generally costly and frequently lead to increase formation of by-products and unwanted side reactions.

Tetrahedron Report No. 553. entitled *The Henry reaction: recent examples* and compiled by F. A. Luzzio, (Tetrahedron 57 (2001) 915-945), provides detailed descriptions of many nitroaldol processes performed with various reactants and catalyst systems. While this article mentions that nitroaldol reactions can be accomplished using water as a solvent, such systems typically include surfactants such as benzyltrimethylammonium hydroxide. Furthermore, although several process schemes list water as a component of the catalyst system, the amounts are not sufficient to form a separate phase, in addition to any organic solvent that is present in the system.

Each of U.S. Pat. Nos. 2,151,517, 5,041,691 and 5,962,737 disclose nitroaldol processes performed in single-phase aqueous solvent systems, i.e., without organic solvent. In particular, U.S. Pat. No. 2,151,517 teaches the nitroaldol reaction of nitroparrafins and aromatic aldehydes in aqueous medium with alkali-metal bisulphate as catalyst. U.S. Pat. No. 5,041,691 describes the reaction of nitroalkanes with formaldehyde, catalyzed by potassium hydroxide. U.S. Pat. No. 5,962,737 describes reaction of nitroethane or nitropropane with substituted benzaldehydes, in the presence of tertiary amines, to accomplish stereospecific synthesis of threo isomers of 2-nitro-1-phenylpropanols.

U.S. Pat. No. 5,750,802 also describes the nitroaldol reaction of nitroalkanes with aromatic aldehydes, in the presence of amine catalysts. This reference teaches that while no additional solvent beyond the amine catalyst is required, common solvents, including those containing water, may be used. No mention, however, is made of a two-phase solvent system— organic and aqueous.

Nitroaldol reactions have even been reported in the absence of any solvent, but again, this required use of surfactants. See A. Bhattacharya and V. C. Purohit, *Environmentally Solvent-Free Processes: Novel Dual Catalyst System in Henry Reaction*, Org. Process Res. & Devel, 2003, 7, pp 254-258.

Successful performance of nitroaldol reactions of aliphatic nitro compounds in aqueous media has also been reported, but required the use of surfactants. See R. Ballini and G. Bosica, *Nitroaldol Reaction in Aqueous Media: An Important Improvement on the Henry Reaction*, J. Org. Chem. (1997) 62, pp 425-427, and R. Bellini, et al., *Recent Developments on the chemistry of aliphatic nitro compounds under aqueous medium*, Green Chem., 2007, 9, pp 823-838.

SUMMARY OF THE INVENTION

The present invention provides a process for producing nitroalcohols by nitroaldol reaction in a reaction system comprising: a $C_1$-$C_{20}$ nitroalkane, a $C_2$ or higher aldehyde, a reaction medium comprising an organic solvent, and a catalyst comprising an amine, where the process comprises adding an amount of an aqueous solvent to the reaction system sufficient to form a separate aqueous phase in the reaction medium. The aqueous solvent is generally not miscible with the organic solvent and may comprise up to 100% water.

The amount of aqueous solvent added is from 10 to 100 mole % relative to the molar amount of aldehyde present in the reaction system. A particularly suitable amount would be from 20 to 40 mole %.

The reaction temperature is between 10° C. and 90° C., and preferably between 60° C. and 70° C.

The nitroalkane may comprise a $C_1$-$C_{12}$ nitroalkane. The aldehyde may comprise an aliphatic $C_2$ or higher aldehyde. The amine catalyst may be a tertiary amine.

BRIEF DESCRIPTION OF THE DRAWINGS

A more complete understanding of the present invention will be gained by reference to the accompanying FIGURE, in which the nitroaldol reaction progress is tracked over time for an embodiment of the present invention and compared to the progress of the same reaction conducted in accordance with the prior art.

DETAILED DESCRIPTION OF THE INVENTION

It has been discovered that adding an aqueous solvent, in an amount sufficient to form a separate aqueous phase, to amine-catalyzed nitroaldol reactions between nitroalkanes and aldehydes increases the reaction rate. This was found to be particularly effective in the preparation of 3-nitro-4-octanol which is a useful chemical intermediate in the preparation of 3-amino-4-octanol. It is expected that the addition of an aqueous solvent to a variety of such "Henry reactions" that occur between nitroalkanes and aldehydes would successfully achieve an increase in reaction rate.

This invention is unique in that it employs a distinct aqueous phase that accelerates the reaction. Prior technology makes use of surfactants in an effort to bring the reactants (nitroalkanes and aldehydes) into contact with water-soluble catalysts such as sodium hydroxide. It has been found that adding water to a previously homogeneous reactant mixture, such that a separate water phase is formed, accelerates the desired reaction. This effect is seen even if the previous homogeneous mixture contained some amount of water from the catalyst, for example. Although the reaction could be conducted in water for example using inorganic bases as catalysts, either with or without a surfactant, the combination of the tertiary amine catalyst and a separate water phase has been found to be even more effective.

Although water has been employed as a solvent in the past, both in addition to organic solvent and in the absence of organic solvent, surfactants were typically required and the reaction medium remained a single phase system. The increase in reaction rate achieved by the process of the present invention is particularly surprising in light of the fact that the reaction mixture has little affinity for water, the reactants are not soluble in water and no surfactant is used. Water is less expensive than the typical catalysts employed and those listed in the prior art. The increased reaction rate decreases the cost to manufacture products derived from this chemistry and the high purity product obtained will reduce the necessity of downstream processing and reduce additional waste disposal costs.

The process of the present invention is suitable for producing nitroalcohols by nitroaldol reaction in a reaction system comprising: a $C_1$-$C_{20}$ nitroalkane, a $C_2$ or higher aldehyde, a two-phase reaction medium comprising an organic solvent phase and a separate aqueous solvent phase, and a catalyst comprising an amine. Typically, where a $C_1$-$C_{20}$ nitroalkane is reacted with a $C_2$ or higher aldehyde in the presence of an amine catalyst, and the reaction medium is an organic solvent, the reaction rate is increased by addition of an amount of an aqueous solvent to the reaction system sufficient to form a separate aqueous phase in the reaction medium. The aqueous solvent should not be miscible with the organic solvent, so that it forms a separate aqueous phase. The aqueous solvent itself may comprise up to 100% water. Other solvents that are not miscible with the reactants may provide a similar result.

Qualitatively speaking, the aqueous solvent should be added in sufficient quantity to form a separate aqueous phase. It is simplest to use an aqueous solvent which comprises 100% water. Because it is desirable to add the minimum amount of water possible, in order to conserve available reactor volume, the upper limit on water is dictated by economic considerations. It has been found that 3.6% water, on a molar basis relative to the aldehyde is insufficient to produce the desired effect in the particular reaction system studied. The limit of solubility is believed to be approximately 6 mole %, depending on the temperature of the reactants.

The suitable amount of aqueous solvent to be added is from 10 to 100 mole % relative to the molar amount of aldehyde present in the reaction system. The amount should be sufficient to form the necessary separate aqueous phase. The best effect has been observed between about 20 and 40 mole % aqueous solvent (relative to the aldehyde). More aqueous solvent, at least to 100% of the aldehyde, is also effective at increasing the rate; however, the aqueous solvent does not participate in the reaction so it is preferred to use less.

The process according to claim 1, wherein the nitroalkane comprises a $C_1$-$C_{12}$ nitroalkane, such as, but not limited to, nitromethane, nitroethane, nitropropane, nitrobutane, etc.

The aldehyde suitable for use in accordance with the present invention contains at least 2 carbon atoms (i.e., "$C_2$ or higher") and may be aliphatic or aromatic. The aliphatic $C_2$ or higher aldehydes are particularly suitable. Higher aldehydes such as acetaldehyde, propionaldehyde, butyraldehyde, cinnamaldehyde, etc., are also expected to be suitable for use in the process of the present invention.

The amine catalyst may be a primary amine, a secondary amine, a tertiary amine, or a combination thereof. Amine catalysts offer several advantages over the previously used inorganic base catalysts, such as NaOH and KOH. One disadvantage of the inorganic bases is that they often promote undesirable side-reactions due to their higher base strength.

Also, inorganic catalysts are arguably more difficult to remove. It is usually important to remove the catalysts. The organic (amine) catalysts may be readily removed by distillation if that is desired. Amine catalysts offer handling advantages since they are typically less corrosive than the inorganic catalysts. While several amines have been used successfully as catalysts in the process of the present invention, tertiary amines and tertiary aminoalcohols have been found to perform particularly well. Other catalysts that are known to promote the nitroaldol reaction are expected to be suitable for use in accordance with the process of the present invention as well.

The order of addition of reactants, catalyst and solvent is not particularly limited. While the order of addition of: nitroalkane, then water, then catalyst, followed finally by the aldehyde, is useful in controlling the heat of reaction, other orders of addition are effective.

The process of the present invention may be conducted at temperatures between 10° C. and 90° C., such as, for example, between 40° C. and 70° C., or even between 60° C. and 65° C. This temperature range provides a balance between faster rate and lower impurity levels. Increasing temperature generally increases the reaction rate; however, undesirable side reactions are sometimes promoted at higher temperatures. The temperature range of 60° C. and 65° C. is believed to provide a balance between rate and purity.

The nitroaldol reactions of the present inventions are typically performed under atmospheric pressure.

It will be understood that the embodiments of the present invention described hereinabove are merely exemplary and that a person skilled in the art may make variations and modifications without departing from the spirit and scope of the invention. All such variations and modifications are intended to be included within the scope of the present invention.

EXAMPLES

Working Example (A)

A reactor vial was filled with 1.2 moles of 1-nitropropane and to this was added 0.4 moles of water (40 mole %) followed by 0.04 moles of N,N-dimethyl-2-amino-2-methyl-1-propanol and an additional 0.065 moles of water. To this blend of nitroalkane/catalyst/water was added 1 mole of valeraldehyde and the reactor vial immediately sealed and placed in a thermostatically controlled temperature bath at 65 C. This is reaction mix A.

The reactor vial was removed from the controlled temperature bath after two hours and the reaction was allowed to proceed at ambient conditions for a total of 24 hours.

Comparative Example (B)

An identical vial as in Example 1 was filled similarly with 1.2 moles of 1-nitropropane, and 0.04 moles of N,N-dimethyl-2-amino-2-methyl-1-propanol with an additional 0.065 moles of water. To this blend of nitroalkane/catalyst/water was added 1 mole of valeraldehyde and the reactor vial immediately sealed and placed in a thermostatically controlled temperature bath at 65 C. This is reaction mix B. The reactor vial was removed from the controlled temperature bath after two hours and the reaction was allowed to proceed at ambient conditions for a total of 24 hours.

Samples were removed from each of the reactor vials at the designated times and they were analyzed by GC for the product of this particular Henry reaction, 3-nitro-4-octanol. The table below provides the numerical results of the GC analysis for each time interval. The chart in FIG. 1 plots the data in the table and shows the relative increase in concentration of the product as a function of reaction time for the two examples, A (working) and B (comparative).

TABLE

| Time (hours) | Working Example A (mole %) | Comparative Example B (mole %) |
|---|---|---|
| 0 | 0 | 0 |
| 2 | 51.67 | 15.21 |
| 3 | 67.72 | 20.69 |
| 5.33 | 80.07 | 36.02 |
| 7 | 79.74 | 48.57 |
| 24 | 82.24 | 80.47 |

What is claimed is:

1. A process for producing nitroalcohols by nitroaldol reaction in a reaction system comprising: a $C_1$-$C_{20}$ nitroalkane, an aliphatic $C_2$ or higher aldehyde, a reaction medium comprising an organic solvent, and a catalyst comprising a tertiary amine, said process comprising:

a) adding from 10 to 100 mole % of an aqueous solvent, relative to the molar amount of aldehyde present in the reaction system, to the reaction system to form a separate aqueous phase in the reaction medium.

2. The process according to claim 1, wherein the aqueous solvent is not miscible with the organic solvent.

3. The process according to claim 2, wherein the aqueous solvent comprises up to 100% water.

4. The process according to claim 1, wherein the amount of aqueous solvent added is from 20 to 40 mole % relative to the molar amount of aldehyde present in the reaction system.

5. The process according to claim 1, wherein the nitroalkane comprises a $C_1$-$C_{12}$ nitroalkane.

6. The process according to claim 1, wherein the reaction system has a temperature between 10° C. and 90° C.

7. The process according to claim 6, wherein the reaction system has a temperature between 60° C. and 70° C.

* * * * *